United States Patent [19]

Moret et al.

[11] Patent Number: 4,880,382

[45] Date of Patent: Nov. 14, 1989

[54] INTEGRATED ORAL HYGIENE SYSTEM

[75] Inventors: Michel A. Moret, Geneve; Pierre J. Jousson, Montchoisy, both of Switzerland

[73] Assignee: Les Produits Associes, LPA SA, Switzerland

[21] Appl. No.: 937,566

[22] Filed: Dec. 3, 1986

[51] Int. Cl.⁴ .............................................. A61C 3/03
[52] U.S. Cl. .................................. 433/118; 433/124; 128/62 A; 132/309
[58] Field of Search ............. 128/62 A, 66; 132/84 A, 132/84 R, 89, 91, 92 R, 92 A, 93; 433/118, 119, 124, 125; 206/369; 15/22 R

[56] References Cited

U.S. PATENT DOCUMENTS

| | | | |
|---|---|---|---|
| 2,911,660 | 11/1959 | Klemas et al. | 128/62 A |
| 3,104,405 | 9/1963 | Perrinjaquet | 15/22 R |
| 3,421,524 | 1/1969 | Waters | 132/92 R |
| 3,636,947 | 1/1972 | Balamuth | 128/66 |
| 3,802,420 | 4/1974 | Moffat et al. | 128/62 A |
| 3,809,977 | 5/1974 | Balamuth et al. | 433/119 |
| 3,967,617 | 7/1976 | Krolik | 128/62 A |
| 3,987,549 | 10/1976 | Robertelli | 433/125 |
| 4,257,433 | 3/1981 | Kwan | 15/22 R |
| 4,319,595 | 3/1982 | Ulrich | 132/92 R |
| 4,432,729 | 2/1984 | Fattaleh | 15/22 R |
| 4,458,702 | 7/1984 | Grollimund | 15/22 R |

Primary Examiner—John J. Wilson
Attorney, Agent, or Firm—Kane, Dalsimer, Sullivan, Kurucz, Levy, Eisele and Richard

[57] ABSTRACT

An integral oral hygiene system which includes an electric toothbrush wherein the brush can be replaced by an interproximal gum stimulator, an interproximal brush or a floss holder, all of which are driven by the toothbrush motor.

3 Claims, 4 Drawing Sheets

INTEGRATED ORAL HYGIENE SYSTEM

FIELD OF THE INVENTION

This invention related generally to an integrated oral hygiene system. More specifically, the invention relates to a novel power driver toothbrush which features interchangeable accessories for various anatomical, pathological and therapeutic needs. The invention also is concerned with the provision in an automatic toothbrush of replaceable accessories, including an interproximal gum stimulator, an interproximal brush, and a power-driven floss holder.

BACKGROUND OF THE INVENTION

As is well known, plaque is one of the primary cause of dental ulcerations and disintegrations of the supporting bone structure of the teeth, and of periodontal diseases. There are many prophylactic dental products which have been proposed for removing the mucous plaque found in the interproximal spaces, and on the proximal surfaces of the teeth. The most commonly used preventative dentistry product is the toothbrush, and more recently, the electric, or power driven tooth brush. A problem arises with such toothbrushes in that they do not sometimes reach into the interproximal spaces, thereby failing to remove the mucous plaque. Removal of the plaque is only one part of a dental hygenic procedure. It has been found that the neutralization of interproximal plaque is an important factor in reducing periodonitis. Brushing and flossing can reduce the duration of the acidogenic challenge. Normal manual flossing with a dental floss with thread made of artificial silk fiber or synthetic fiber while beneficial is somewhat restricted to the number or frequency of manual manipulations.

OBJECTS AND SUMMARY OF THE INVENTION

One object of the invention is to provide an integrated system which will permit the carrying out of an oral hygiene program.

Another object of the invention is to provide a dental care system which will efficiently eliminate food particles from retention zones in the teeth.

A still further objective of the invention is to provide an improved automatic toothbrush assembly which is at once an effective, pleasant, safe and reliable tool for plaque removal, reduction of gum inflammation and for polishing of tooth enamel. Another object of the invention within the generic scope thereof, is to provide a novel interproximal brush and gum stimulator for attachment to an automatic toothbrush.

An additional object of the invention is to provide a power-driven flossing device for giving optimum motion to the dental floss while increasing the frequency of moement to optimize plaque removal.

Another object of the invention is to provide a novel dental floss covered by colored wax along its entire length so as to indicate parts thereof which have been used by the disappearance of the colored wax.

These objects are achieved in accordance with the invention by means of an integrated system based on an automatic toothbrush having a power handle and to which may be removably secured a toothbrush, specially designed for removing plaque from inter-proximal spaces, an interproximal gum stimulator and a dental floss holder for imparting to a dental floss a partly hyperboloidal revolution. In a preferred embodiment of the invention, the dental floss can be of novel design and be entirely coated with a removable colored wax coating to indicate the portions thereof already used and/or passed through a fluoridated liquid colored green.

The above mentioned accessories are intended to be used after regular use of an automatic toothbrush as supplementary cleaning means to remove plaque in interdental spaces and to stimulate the gums. The massage in question can be varied from a surface massage to the gums to promote keratinization to a deep massage to accelerate blood circulation therein.

BRIEF DESCRIPTION OF THE DRAWINGS

In the above figures the same reference characters refer to the same or like parts.

DESCRIPTION OF PREFERRED EMBODIMENTS

Figure 1:
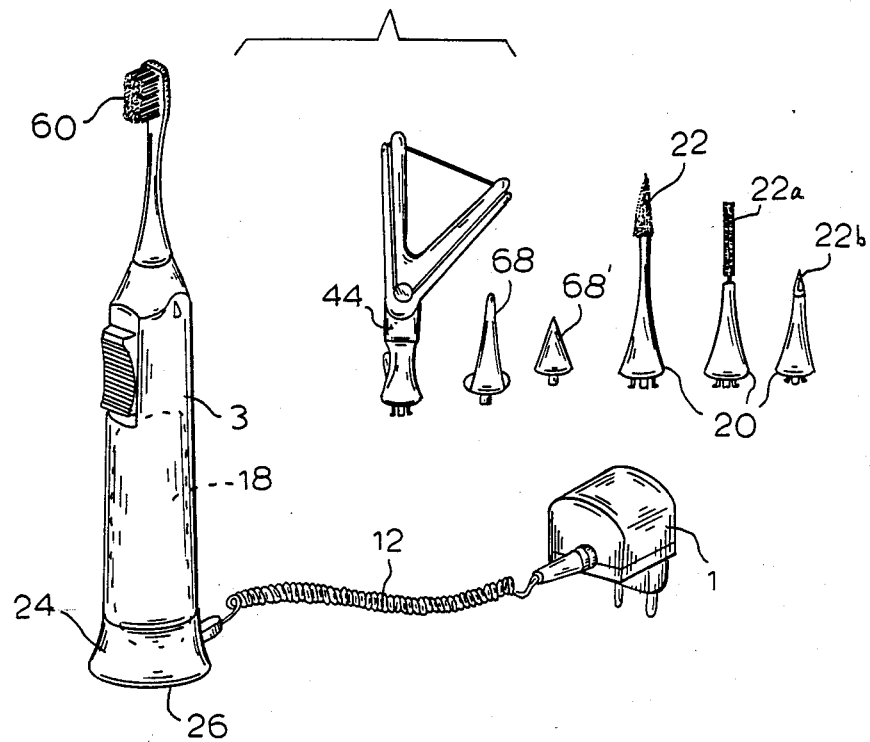
FIG. 1 is a perspective view showing the system of the invention.
Figure 4:
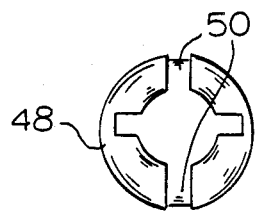
FIG. 4 is a cross-sectional view, taken along line 4—4 of FIG. 2 and showing the outer end of the connection uniting the floss holder to the power shaft.
Figures 2, 3:
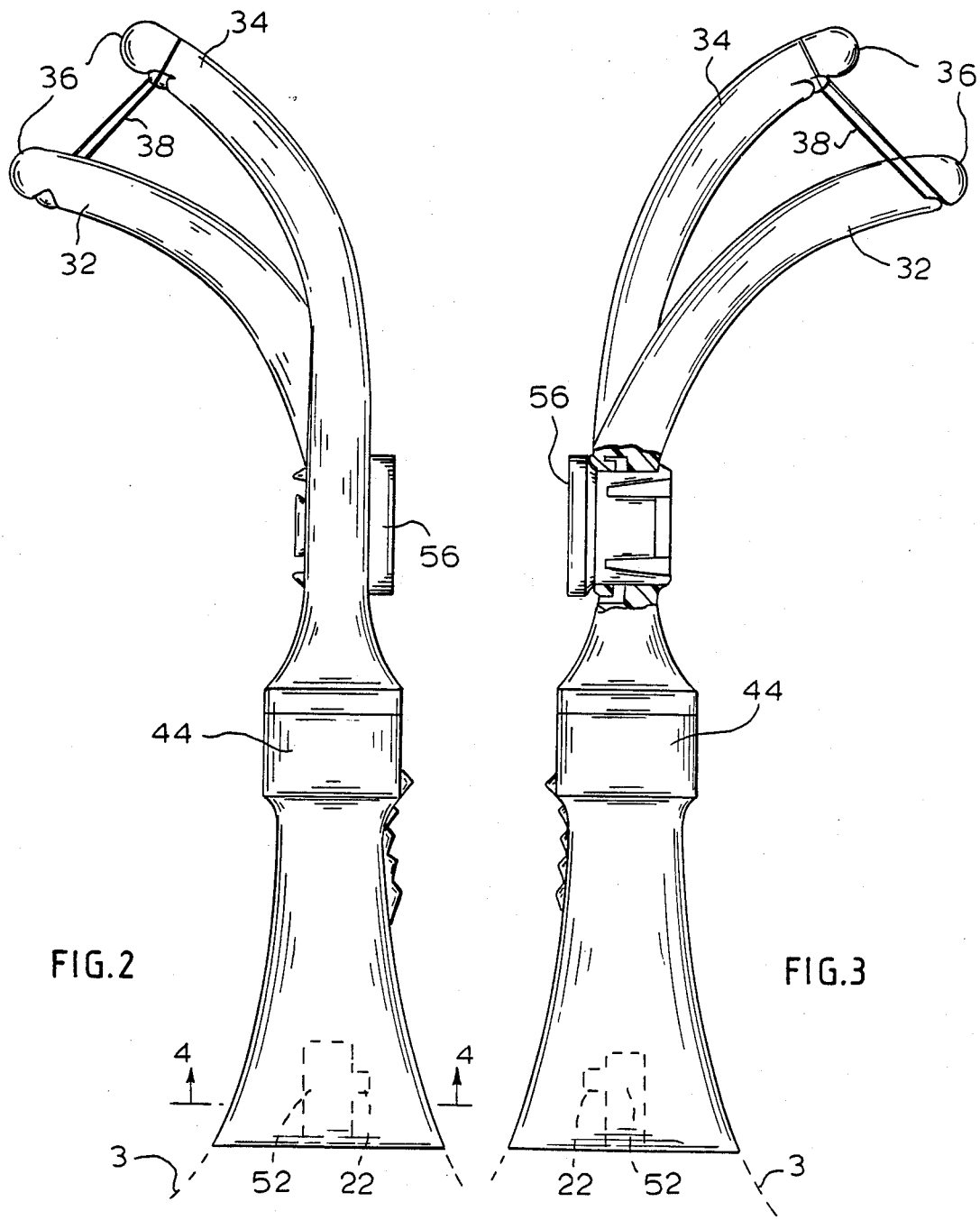
FIG. 2 is a side elevational view of the dental floss holder.
FIG. 3 is a similar view, partly in section of the active part of the floss holder.

Referring descriptively to the drawing:

The apparatus of the invention contemplates any type of automatic or power driven toothbrush including electrically or battery or rechargeably-battery operated apparatus of this type. Thus it may comprise a plug-in transformer 1 connected to electric toothbrush 3 by a coiled cord 12. A motor (18) activated by switch (19) for varying the output speed of the shaft (52) which has thereon key (22). In operation, the motor causes oscillation of the shaft 52 above its longitudinal axis and consequently rotational oscillation of toothbrush 14 above this axis.

The casing of the toothbrush forming the handle may be of any suitable thermoplastic material and the toothbrush casing can be of any desired shape which will not interfere with its handling or operation. It will have at its lower extremity a mirror (26) which makes it possible for the user of the apparatus to view his teeth, so as to continue or stop brushing thereof.

Referring now to FIGS. 2-5, a dental floss holder (30) in accordance with the invention comprises a pair of curved tines (32 and 34) with tine (32) being smaller than tine (32). The proximal end of each tine has a rounded surface (36) around which dental floss (38) is wound for use. The shorter tine (32) is bent at a much greater angle than longer tine (34). The lower end of base (44) has a substantially cruciform inner arrangement of compartments with slot (50) being open so as to facilitate introduction therein of key or pin (22) of shaft (52). It will be understood that the floss holder is molded from a suitable rigid plastic material to avoid that during use the fork or tines holding the dental floss bends and allows the floss to get out from its guiding channels (54). A button (56) which is spaced slightly from the upper surface of the floss holder to permit tightening of the loop of floss therearound.

In order to obtain an effective cleaning action on the part of the floss and without irritating the gum, the dental floss holder must be shaped and disposed as drawn in order to have the floss (38) describe in the space between the tines (32 and 34) a portion of a hyperboloid revolution. The compound movement optimizing a cleaning but at the same time will not cut gums. The lower end of the base (44) is friction fitted on the end of shaft (52). A rotational oscillating motion is imparted to the floss holder (30) above the longitudinal axis. This motion has a frequency which will range between 40 to 60 c/s. The motion of the dental floss holder must be very small and preferably only about one to two mm at the dental floss level, which means a very small angle of oscillation of the motor shaft of only a few degrees.

Figure 5:
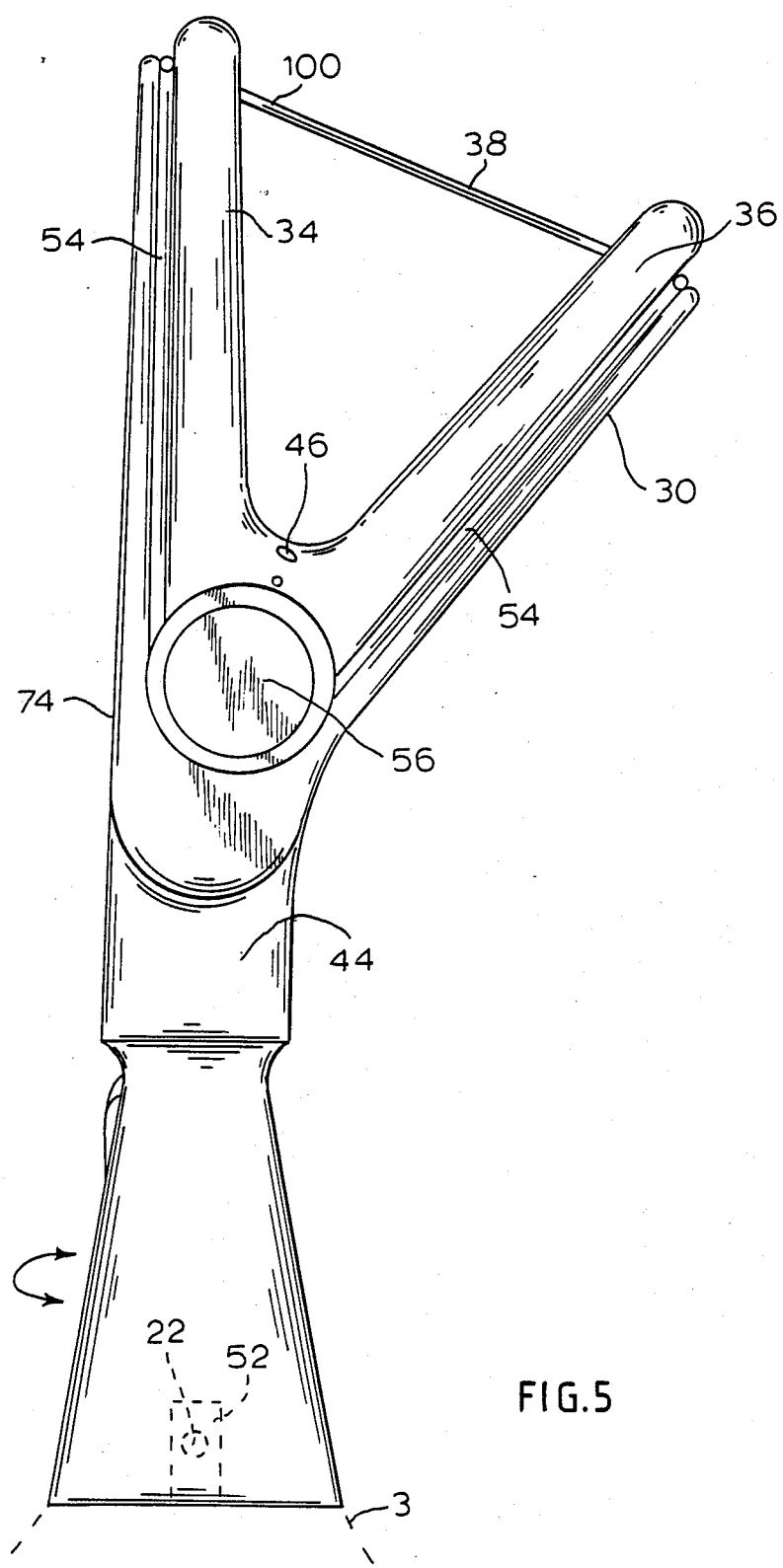
FIG. 5 is a further elevational view of the floss holder shown in enlarged detail.

The floss of the present invention can have thereon a coating of wax which disappears when the floss is used to make clearly apparent the portions of the floss already used. This is achieved by placing a coating of wax to which has been added a coloring pigment which rubs off when using the floss. This coating is shown in FIG. 5 and is referenced 100. The pigment may be incorporated in the wax in any manner known per se. The color coding, such as a blue wax coating, makes it apparent to the user which portions of the floss have been used, so that he will not reuse these portions. This therefore, minimizes passage of harmful bacteria from one interdental space to another space.

Figure 6:
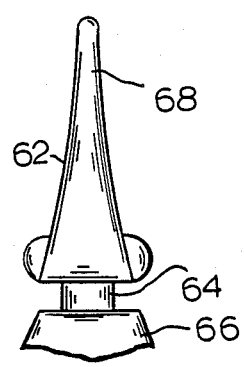
FIG. 6 is a side view of the interproximal gum stimulator.
Figure 7:
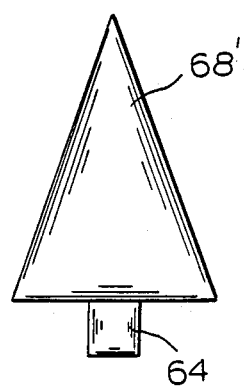
FIG. 7 is a side view of a modified pyramid-shaped tip for use in the assembly of FIG. 6.
Figure 8:
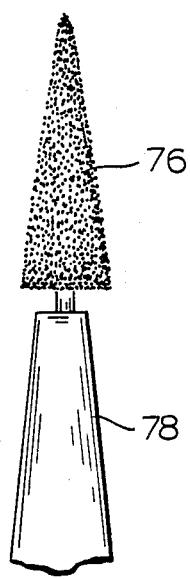
FIG. 8 is a side view partially in section of an interproximal brush in accordance with the invention.

Another accessory in the present system is shown in FIG. 6. This accessory is an interproximal gum stimulator (62), which is formed of a rubber-like material or a soft plastic material, and shaped like a tiny cylindrical or slightly conical brush which describes an axial oscillating motion. The stimulator has a threaded portion (64) at its lower end, which is threaded into connector (66) the base of which is snap fitted on the shaft (52) and keyed by key 22. The oscillating axis of the motor shaft is aligned with the axis of the brush. The general shape of the stimulator tip (68) can be as shown in FIG. 6. But the tip 68 can be more or less sharp-pointed if desired, according to the interdental space. Additionally the tip (68') extending from thereabout portion (64') can be given a pyramidal shape as shown in FIG. 7 to give a greater massaging efficiency to the gums. Where the users have very bad gum conditions, it is recommended that they start with a very soft tip (68) and to change to a harder one when the gum conditions have improved. To differentiate the hardness of the tips, the various tips can be colored differently, according to hardness.

FIG. 9 shows an interproximal brush (76) and conical holder (78) which fits on drive shaft 52 for oscillating thereforth. Brush 76 is made of twisted wires having an inner end received in the holder (78) and preferably anchored therein. Brush 76 removes plaque from interproximal spaces and massages the gum. This brush makes an axial oscillating motion which insures a better cleaning and plaque removal and does not irritate the gums. The bristles also can have tufts of radially extending material which decrease in length toward the front of the brush.

Thus, an integrated system is provided that will facilitate a complete oral hygiene program. A single automatic toothbrush which generates a rotary oscillation output, the front and rear surfaces of the tooth may be cleaned with the brush 14, the interproximal surfaces cleaned by brush 76, flossing accomplished by floss 38 and gum massage by any of the foregoing together with tip 68.

Use of the present invention is indicated for the prevention of dental plaque formation and removal of existing plaque. It is also intended for the stimulation of gingival epithelium, producing thickening of the tissue or keratinization and increasing its resistance. The apparatus also is indicated for the reduction of gingival inflammation. It complements the professional treatment of periodontal disease and can be used to polish dental enamel without abrading the same. Automatic flossing is achieved as well as interproximal teeth cleaning or gum massinging stimulation.

In a preferred embodiment of the invention, the toothbrush motor provides about 3000 oscillating movement per minute expedite cleaning and massaging. This insures dental plaque removal from risk areas (interdental spaces and around the gingival margin), and massaging if the gums efficiently and automatically.

What is claimed is:
1. An integrated oral hygiene system for facilitating a complete oral hygiene program comprising in combination:
   a handle having a top end and a bottom end, a motor housed in said handle, and having a shaft having a longitudinal axis protruding therefrom, said shaft having a longitudinal axis and being rotationally oscillated about said longitudinal axis responsive to said motor;
   a plurality of accessories interchangeably mountable on said shaft and adapted to be used interchangeably and frequently;
   said accessories comprising:
   a toothbrush having bristles and a holder adapted to fit on the shaft;
   a dental floss holder having one end adapted to fit on said shaft and another end divided into a pair of forks;
   said forks having extremities bent along different axes having floss stretched therebetween;
   an interproximal brush, rotationally symmetric about said longitudinal axis, having a holder removably mounted on said shaft; and
   a gum stimulator, rotationally symmetric about said longitudinal axis, mountable upon said shaft.

2. The apparatus according to claim 1, wherein said motor provides a frequency of oscillating motion ranging between 40 to 60 c/s.

3. A method of obtaining oral hygiene comprising the steps of:
   utilizing an integrated oral hygiene system comprising:
   a handle having a top end and a bottom end, a motor housed in said handle, and having a shaft having a longitudinal axis protruding therefrom, said shaft having a longitudinal axis and being rotationally oscillated about said longitudinal axis responsive to said motor;
   a plurality of accessories interchangeably mountable on said shaft;
   said accessories comprising:
   a toothbrush having bristles and a holder adapted to fit on the shaft;

a dental floss holder having one end adapted to fit on said shaft and another end divided into a pair of forks;

said forks having extremities bent along different axes having floss stretched therebetween;

an interproximal brush, rotationally symmetric about said longitudinal axis, having a holder removably mounted on said shaft; and a gum stimulator, rotationally symmetric about said longitudinal axis, mountable upon said shaft, and using said accessories interchangeably, frequently and in any sequence.

* * * * *